(12) United States Patent
Andes et al.

(10) Patent No.: US 6,648,957 B1
(45) Date of Patent: Nov. 18, 2003

(54) MULTILAYER NACREOUS PIGMENT

(75) Inventors: Stephanie Andes, Hanau (DE); Gerald Fuchs-Pohl, Weiterstadt (DE); Gerhard Pfaff, Munster (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/889,388

(22) PCT Filed: Jan. 7, 2000

(86) PCT No.: PCT/EP00/00071
§ 371 (c)(1),
(2), (4) Date: Dec. 4, 2001

(87) PCT Pub. No.: WO00/42111
PCT Pub. Date: Jul. 20, 2000

(30) Foreign Application Priority Data

Jan. 18, 1999 (DE) ......................................... 199 01 609

(51) Int. Cl.$^7$ ............................................... C04B 14/00
(52) U.S. Cl. ...................... 106/415; 106/404; 106/418; 106/425; 106/430; 106/431; 106/434; 106/435; 106/438; 106/439; 106/441; 106/442; 106/453; 106/454; 106/456
(58) Field of Search ................................ 106/415, 404, 106/418, 425, 430, 431, 434, 435, 438, 439, 440, 441, 442, 453, 456, 454

(56) References Cited

U.S. PATENT DOCUMENTS

| | | | | |
|---|---|---|---|---|
| 5,573,584 A | * | 11/1996 | Ostertag et al. | ............. 101/491 |
| 5,958,125 A | * | 9/1999 | Schmid et al. | ............... 106/415 |
| 6,045,914 A | * | 4/2000 | Sullivan et al. | ............... 106/415 |

FOREIGN PATENT DOCUMENTS

| | | | |
|---|---|---|---|
| DE | 19618569 | 11/1997 | |
| DE | 19707806 | 9/1998 | |
| WO | WO 93/08237 | * 4/1991 | ............. C09C/1/00 |
| WO | 92/08237 | 4/1993 | |

* cited by examiner

*Primary Examiner*—C. Melissa Koslow
*Assistant Examiner*—Shalie Manlove
(74) *Attorney, Agent, or Firm*—Millen, White, Zelano, Branigan, P.C.

(57) ABSTRACT

Multilayer pearl lustre pigment on the basis of a platelet-shaped substrate comprising a material of low refractive index in the range from 1.35 to 1.8, which comprises at least
(i) one first layer comprising a material having a refractive index of more than 1.8,
(ii) optionally, a second layer comprising a material of low refractive index in the range from 1.35 to 1.8,
(iii) a semitransparent metal layer which is applied to the substrate or to the layers (i) or (ii), and
(iv) if desired, an aftercoating, the substrate being platelet-shaped silicon dioxide, aluminium oxide, boron oxide or magnesium fluoride.

18 Claims, No Drawings

MULTILAYER NACREOUS PIGMENT

The invention relates to a multilayer pearl lustre pigment having a pronounced colour flop, based on a platelet-shaped substrate comprising a material of low refractive index in the range from 1.35 to 1.8.

Multilayer pigments which exhibit an angle-dependent colour change between two or more intensive interference colours are known.

For instance, U.S. Pat. No. 4,434,010 describes a multilayer interference pigment consisting of a central layer of a reflective material (aluminium) and alternating layers of two transparent, dielectric materials of high and low refractive index, for example titanium dioxide and silicon dioxide, on either side of the central aluminium layer. In a further embodiment of the pigment, the layers following the central aluminium layer are formed by magnesium fluoride and chromium. This pigment exhibits an intensive colour flop from green to purplish red.

EP 0 753 545 describes goniochromatic lustre pigments based on transparent, non-metallic, platelet-shaped substrates, which have at least one layer stack comprising a colourless coating with a refractive index n≦1.8 and a reflective, selectively or non-selectively absorbing coating which is at least partly transparent to visible light, and which also have, if desired, an external protective layer in addition.

These pigments have the disadvantage that they are produced by a technically very complex and costly process, for example by chemical vapour deposition (CVD) or physical vapour deposition (PVD) techniques. Further disadvantages are the frequent difficulty in reproducing the pigments in the desired product quality, and their deficient weathering stability.

It is the object of the present invention to provide an essentially transparent interference pigment having strong interference colours and/or a high angular dependency of the interference colours and featuring advantageous applications properties, which at the same time is simple to produce.

This object is achieved in accordance with the invention by a multilayer pearl lustre pigment on the basis of a platelet-shaped substrate comprising a material of low refractive index in the range from 1.35 to 1.8, which comprises at least (i) one first layer comprising a material having a refractive index of more than 1.8,
(ii) optionally, a second layer comprising a material of low refractive index in the range from 1.35 to 1.8,
(iii) a semitransparent metal layer which is applied to the substrate or to the layers (i) or (ii), and
(iv) if desired, an aftercoating.

If the semitransparent metal layer forms the outer layer of the pigment, it is also possible for layers of high and low refractive index to follow. Before the metal layer is applied, the first and second layers may also be repeated.

This object is further achieved, in accordance with the invention, by a process for producing the pigment of the invention by applying a precursor of the substrate material as a thin film to a smooth surface,
solidifying the liquid film by drying,
detaching the dried film and treating it, if desired, with an acid,
washing the resultant substrate particles and resuspending them in a coating solution,
coating the substrate particles with two or more layers of metal oxides or metals, and
aftercoating the resultant pigment.

In addition to the purely colouristic applications, the pigments of the invention can also be considered for functional applications. Examples of these are as pigments for the security sector, e.g. the printing of items of value and of security, as pigments with specific IR reflection, e.g. for glasshouse films, and as pigments for the laser marking of plastics.

The invention additionally provides for the use of the pigments of the invention in paints, varnishes, printing inks, plastics, ceramic materials, glasses and cosmetic formulations. For these purposes they may also be employed as mixtures with commercially customary pigments, examples being organic and inorganic absorption pigments, metal-effect pigments and LCP pigments.

The pigments of the invention are based on platelet-shaped substrates. These substrates may consist of silicon dioxide, silicates, boron oxide, borates, aluminium oxide, glass, magnesium fluoride or other transparent and stable materials capable of taking on soluble or insoluble colorants.

Precursors employed for the production of the substrates are solutions of organic or inorganic compounds of the metals aluminium, silicon, potassium or sodium with borates, aluminates, poly- and/or metaphosphates, silicates or mixtures thereof. A preferred precursor is waterglass.

The platelet-shaped substrate particles have a thickness of between 0.05 and 5 $\mu$m and, in particular, between 0.2 and 2 $\mu$m. The extent in the other two dimensions is between 1 and 250 $\mu$m, and, in particular, between 2 and 100 $\mu$m.

Insoluble colorants incorporated into the substrate may be pigment particles whose dimensions are markedly smaller than the thickness of the substrate. The particle size of the commercially customary pigments must therefore be adapted to the desired layer thickness of the substrate. The term pigment particles here should be interpreted broadly and embraces white, black, colour and fluorescent pigments.

Suitable inorganic pigments are white pigments such as titanium dioxide, barium sulphate or zinc oxide, examples being Titandioxid 2310 (manufacturer: Kronos), Titandioxid R-D (manufacturer: Bayer) and Titandioxid R-506 (manufacturer: Sachtleben).

Suitable black pigments are magnetite or pigment black, an example being Farbrub FW 200 (Degussa).

Suitable colour pigments are iron oxide or chromium oxide, mixed-phase oxides such as (Ti, Cr, Sb)$O_2$, $CoAl_2O_4$ (Thenard's Blue), $ZnAl_2O_4$ (Rinman's Green), $(Fe,Cr)_2O_3$ and also sulphides, for example CdS.

Also suitable are inorganic fluorescent pigments, such as fluorescent silver-doped zinc oxide, phosphorescent copper-doped zinc sulphide, or ultramarine pigments.

Suitable organic pigments are azo pigments, anthraquinone pigments, indigo or thioindigo derivatives, diketopyrrolopyrrole pigments, perylene pigments or phthalocyanine pigments. Particularly suitable red pigments are Paliogen Maron L3920 (manufacturer: BASF), DPP-Irgazin Red BO (manufacturer: Ciba), Chinquaisia Margenta RT355D (manufacturer: Ciba), Hostaperm Red E2B70 (manufacturer: Hoechst—Clariant), Sicotrans Red L2817 (manufacturer: BASF), Carmine Red, Thioindigo, DC Red 6, also known as Lithol Rubin 13, and DC Red 33, also known as Acid Fuchsine. Particularly suitable blue pigments are Hostaperm Blue AFL (manufacturer: Hoechst—Clariant), Irgazin Blue A3RN (manufacturer: Ciba), Paliogen Blue L6470 (manufacturer: BASF), Prussian Blue, and FDC Blue 1, also known as Brilliant Blue. Particularly suitable green pigments are Monastral Green 64 Special (manufacturer: Zeneca—ICI), Hostaperm Green 8G (manufacturer: Hoechst—Clariant), DC Green 5, also known as Alizarin Cyanin Green F and particularly suitable yellow pigments are Irgazin Yellow 5GTL (manufacturer: Ciba), Irgacolor Yellow 2GLMA (manufacturer: Ciba), FDC Yellow 5, also known as tartrazine, and FDC Yellow 6, also known as Sunset Yellow.

To aid dispersion of the pigment particles in the precursor it is in many cases advantageous to add wetting agents, for example Hydropallat 884 (manufacturer: Henkel). Neither the type nor the amount of the wetting agent added is critical, although in general the proportion of wetting agent is not more than 2% by weight, based on the dispersion.

The weight fraction of the incorporated pigment particles, based on the weight of the uncoated substrate, is between 0.5 and 40% and, in particular, between 5 and 25%. Further details can be found in European Patent 0 608 388.

The substrate may alternatively comprise a soluble colorant as the colorant. The term "soluble colorant" means either a chromophoric metal oxide, for example iron oxide, chromium oxide or cobalt oxide, or a soluble organic dye.

Generally suitable for the colouring of the substrate are chromophoric compounds of the metals titanium, vanadium, chromium, manganese, iron, cobalt, nickel and copper, preferably compounds of cobalt, copper, iron and chromium. They are added as soluble compounds to the precursor of the substrate. The result is a coloured, transparent substrate having a colour scale similar to that of coloured, transparent glass. Adding iron compounds, for example, gives reddish brown shades, adding chromium compounds green shades, and adding cobalt compounds blue shades.

Soluble organic dyes which can be employed include alkali-soluble hydroxyanthraquinone dyes or acidic azo dyes.

The soluble colorant is present in the uncoated substrate in a proportion of from 0.01 to 50% by weight, preferably from 1 to 30% by weight. Further details can be found in EP 0 608 388.

Suitable layer material for the layer having a refractive index of more than 1.8 comprises all materials of high refractive index which are known to the person skilled in the art and can be applied permanently and in film-like manner to the substrate particles. Particularly suitable are metal oxides or metal oxide mixtures, such as $TiO_2$, $Fe_2O_3$, $ZrO_2$, $ZnO$, $SnO_2$, or compounds of high refractive index, such as iron titanates, iron oxide hydrates, titanium suboxides, chromium oxide, bismuth vanadate, cobalt aluminate, and also mixtures and/or mixed phases of the said compounds with one another or with other metal oxides. Metal sulphides, metal nitrides and metal oxynitrides are also suitable.

The thickness of the layer (i) is 10–550 nm, preferably 15–400 nm and, in particular, 20–350 nm. Suitable layer materials for the layer of low refractive index (ii) are preferably metal oxides and/or the corresponding oxide hydrates, such as $SiO_2$, $Al_2O_3$, $AlO(OH)$, $B_2O_3$ or a mixture of the said metal oxides, or $MgF_2$. The thickness of the layer is 10–1000 nm, preferably 20–800 nm and in particular, 30–600 nm.

Alternatively, the material of low refractive index employed can comprise polymers, such as acrylates. The monomers used have a molecular weight of from 200 to 1000 and are available as mono-, di- or triacrylates. In terms of functional groups, they are available as hydrocarbons, polyols, polyethers, silicones or fluorinated Teflon-like monomers. These monomers carl be polymerized by electron beams or UV rays. The layers obtained possess a temperature stability of up to 250° C. The refractive indices of the acrylate layers lie within the range from 1.35 to 1.60.

Further details can be found in David G. Shaw and Marc G. Langlois: Use of a new high speed acrylate deposition process to make novel multilayer structures, MRS Conference in San Francisco 1995; A new high speed process for vapour depositing fluoro and silicone acrylates for release coating applications, Conference of the Society of Vacuum Coaters in Chicago, Ill., 1995.

The layer thickness of the polymer layer is set at values between 20 and 700 nm, preferably between 60 and 500 nm.

The metal layers (iii) consist of metals, such as aluminium, chromium, nickel, chromium-nickel alloys or silver. Chromium and aluminium are preferred here, since they are easy to deposit. The layer thickness of the metal layers is set at from 5 to 20 nm in order to obtain semitransparency. Alternatively, materials such as graphite or titanium nitride can be employed as semitransparent reflector layers.

The pigments of the invention also include additional colorants in the metal oxide coating. If, for example, particles of carbon black are used, then particle sizes of from 5 to 200 nm, and, in particular, from 10 to 100 nm are used. Pigments of this kind, which contain preferably carbon black particles in layers of titanium dioxide, iron oxide, tin oxide, chromium oxide and zinc oxide, are described in EP 0 499 864.

In addition, the pigments of the invention may also comprise particles of titanium dioxide, aluminium oxide, silicon dioxide, tin dioxide, magnesium oxide, zinc oxide, cerium dioxide, tungsten oxide, molybdenum oxide, zirconium oxide, or else mixed oxides, such as $Cr_2FeO_4$, $CoAl_2O_4$ or $NiAl_2O_4$, in the metal oxide layer.

Instead of inorganic pigment particles it is also possible for organic pigment particles to be present in the metal oxide layer, in which case particular preference is given to temperature-stable organic pigments. Organic pigment particles used are preferably phthalocyanines, products of laking basic dyes with heteropolyacids, and anthraquinones, phenazines, phenoxazines, diketopyrrolopyrroles or perylenes. In principle, all pigments which have been described for incorporation into the substrate can also be incorporated into the coating of the pigment of the invention. The incorporation of small particles of metal oxide or organic pigment having an average size of from 10 to 40 nm into the cavities of the metal oxide coating brings about a marked increase in the hiding power and in the lustre, in association with a high level of homogeneity of the coating in comparison to pigments obtained by coprecipitation. The hiding power and, in the case of coloured pigment particles, the observation-angle-dependent absorption colour of the pigments of the invention can be varied within a wide range by way of the concentration of the pigment particles incorporated. The mass fraction of incorporated pigment particles, based on the coating, lies between 0.5 and 30% and, in particular, between 2 and 20%. Further details of pigments which comprise pigment particles in the coating can be found in DE 41 40 295.

The finished pigment is subjected to an aftercoating or aftertreatment (iv), which increases further the light stability, weathering stability and chemical stability, or which facilitates the handling of the pigment, especially its incorporation into various media. Suitable aftercoatings or aftertreatments are, for example, the processes described in DE-C 22 15 191, DE-A 31 51 354, DE-A 32 35 017 or DE-A 33 34 598.

The additionally applied substances account for only from about 0.1 to 5% by weight, preferably from about 0.5 to 3% by weight, of the overall pigment.

The number and thickness of the layers is dependent on the desired effect and on the substrate used. The number of layers is limited by the economics of the pigment. If the substrate used is $SiO_2$ platelets, which in accordance with the process described in EP 0 608 388 are produced on a continuous belt, it is possible to obtain particularly well-defined interference effects, since in contrast to mica these $SiO_2$ platelets possess a uniform layer thickness. The reflection spectrum or transmission spectrum of such a pigment features finer and more precisely harmonizable structures than the spectrum of a corresponding pigment which is based on a substrate having a broad thickness distribution, such as mica, for example.

In accordance with EP 0 608 388 the $SiO_2$ platelets are produced on a continuous belt by solidification and hydrolysis of a waterglass solution.

The metal oxide layers are preferably applied by wet-chemical means, it being possible to employ the wet-chemical coating techniques developed for the production of pearl lustre pigments; such techniques are described, for example, in ,DE 14 67 468, DE 19 59 988, DE 20 09 566, DE 22 14 545, DE 22 15 191, DE 22 44 298, DE 23 13 331, DE 25 22 572, DE 31 37 808, DE 31 37 809, DE 31 51 343, DE 31 51 354, DE 31 51 355, DE 32 11 602, DE 32 35 017 or else in further patent documents and in other publications.

For coating, the substrate particles are suspended in water and the suspension is admixed with one or more hydrolysable metal salts at a pH suitable for the hydrolysis, this pH being chosen such that the metal oxides and/or metal oxide hydrates are deposited directly on the particles without instances of secondary precipitation. The pH is normally held constant by simultaneous metered addition of a base. Subsequently, the pigments are separated off, washed and dried and, if desired, calcined, it being possible to optimize the calcination temperature in respect of the particular coating present. If desired, the pigments can be separated off, dried and, if desired, calcined following the application of individual coatings, before then being resuspended in order to apply the further layers by precipitation.

In addition, coating can also be carried out by gasphase coating in a fluidized-bed reactor, it being possible to employ, accordingly, the techniques proposed in EP 0 045 851 and EP 0 106 235 for the production of pearl lustre pigments.

For the application of titanium dioxide layers, preference is given to the technique described in U.S. Pat. No. 3,553,001.

An aqueous titanium salt solution is added slowly to a suspension, heated to about 50–100° C., especially 70–80° C., of the material to be coated, and a substantially constant pH of about 0.5–5, in particular about 1.5–2.5, is maintained by simultaneous metered addition of a base, such as aqueous ammonia solution or aqueous alkali metal hydroxide solution, for example. As soon as the desired layer thickness of the $TiO_2$ precipitate is reached, the addition of the titanium salt solution and of the base is stopped.

This technique, which is also referred to as the titration technique, is notable for the fact that it avoids an excess of titanium salt. This is achieved by supplying to the hydrolysis per unit time only that quantity of titanium salt solution which is required for uniform coating with the hydrated $TiO_2$ and can be received per unit time by the available surface area. Consequently, no hydrated titanium dioxide particles are produced that are not precipitated on the surface to be coated.

For the application of the silicon dioxide layers, the following technique can be employed: a sodium waterglass solution is metered into a suspension, heated to about 50–100° C., especially 70–80° C., of the material to be coated. The pH is held constant at from 4 to 10, preferably from 6.5 to 8.5, by simultaneous addition of 10% hydrochloric acid. Following the addition of the waterglass solution, stirring is continued for 30 minutes.

The individual layers can also be produced in accordance with known techniques by sputtering metals, such as aluminium or chromium, or alloys, such as Cr—Ni alloys, and also metal oxides, for example titanium oxide, silicon oxide, or indium-tin oxide, or by thermal evaporation of metals, metal oxides or acrylates. Preference is given to a vacuum belt coating as discribed in DE 197 07 805 and in DE 197 07 806 for the production of interference pigments.

What is claimed is:

1. A multilayer pearl lustre pigment comprising a platelet-shaped substrate substantially of a material having a low refractive index in the range from 1.35 to 1.8, and selected from silicon dioxide, aluminium oxide, boron oxide or magnesium fluoride, having thereon:
   (i) one first layer comprising a material having a high refractive index of more than 1.8,
   (ii) optionally, a second layer comprising a material of a low refractive index in the range of 1.35 and 1.8; and
   (iii) a semi-transparent metal layer which is applied to the substrate or to the layers (i) or (ii).

2. A pearl lustre pigment according to claim 1, wherein the material of high refractive index is $TiO_2$, $ZrO_2$, $Fe_2O_3$, $Cr_2O_3$, ZnO or a mixture of these oxides or an iron titanate, an iron oxide hydrate, a titanium suboxide or a mixture and/or mixed phase of these compounds.

3. A pearl lustre pigment according to claim 1, wherein the material of low refractive index is $SiO_2$, $Al_2O_3$, AlOOH, $B_2O_3$, $MgF_2$ or an acrylate, and optionally, alkali metal oxides or alkaline earth metal oxides present as additional constituents.

4. A process for producing the pigment according to claim 1, comprising:
   applying a precursor of the substrate material as a thin film to a continuous belt,
   solidifying the liquid by drying,
   detaching the dried film and treating it, optionally with an acid,
   washing the resultant substrate particles and resuspending them in a coating solution, and
   coating the substrate particles with at least two or more layers of metal oxides or metals, with the proviso that at least one layer has a high refractive index of more than 1.8 and at least one layer is a semi-transparent metal layer.

5. A process according to claim 4, wherein the precursor employed is a solution of organic or inorganic compounds of the metals aluminum, silicon, potassium or sodium with borates, chlorides, aluminates, poly- and/or meta-phosphates, silicates or mixtures thereof.

6. A process according to claim 4, wherein the precursor is waterglass.

7. A process according to claim 4, wherein colorants are added to the precursor, either the colorant being dispersed or dissolved in the precursor prior to application to the belt, or the components being applied separately to the belt by way of two or more nozzles.

8. A process according to claim 4, wherein prior to or during application to the continuous belt, particles of an organic or inorganic pigment having dimensions smaller than the thickness of the substrate, are dispersed in the precursor.

9. A process according to claim 8, wherein the dispersed amount of pigment particles is from 0.01 to 99% by weight, based on the precursor.

10. A process according to claim 4, wherein following drying of the substrate to be coated the layers are applied in a fluidized-bed reactor by CVD and/or PVD.

11. A paint, printing ink, plastic, cosmetic, ceramic, glass or polymer film pigmented with a pigment according to claim 1.

12. A laser-markable plastic comprising a pigment according to. claim 1.

13. A pearl lustre pigment according to claim 1, wherein the pigment additionally contains an aftercoating or aftertreatment, which increases the stability or facilitates the handling of the pigment.

14. A process according to claim 4, wherein the pigment is additionally aftercoated or aftertreated, thereby increasing the stability or facilitating the handling of the pigment.

15. A process according to claim 9, wherein the dispersed amount of pigment particles is from 1 to 30% by weight, based on the precursor.

16. A pearl lustre pigment according to claim 1, wherein the platelet shaped substrate has a thickness between 0.05 and 5 $\mu$m and an extent in the other two directions between 1 and 250 $\mu$m.

17. A pearl lustre pigment according to claim 16, wherein the platelet shaped substrate has a thickness between 0.2 and 2 $\mu$m and an extent in the other two directions between 2 and 100 $\mu$m.

18. A pearl lustre pigment according to claim 1, wherein the material of high refractive index is chromium oxide, bismuth vanadate, cobalt aluminate, a metal sulphide, a metal nitride, a metal oxynitride or a mixture and/or mixed phase of these compounds.

* * * * *